US009333203B2

(12) United States Patent
Tuiten et al.

(10) Patent No.: US 9,333,203 B2
(45) Date of Patent: *May 10, 2016

(54) PHARMACEUTICAL FORMULATIONS AND USES THEREOF IN THE TREATMENT OF FEMALE SEXUAL DYSFUNCTION

(75) Inventors: Jan J. A. Tuiten, Almere (NL); Johannes M. M. Bloemers, Almere (NL)

(73) Assignee: EB IP LYBRIDO B.V., Almere (NL)

( * ) Notice: Subject to any disclaimer, the term of this patent is extended or adjusted under 35 U.S.C. 154(b) by 1116 days.

This patent is subject to a terminal disclaimer.

(21) Appl. No.: 12/084,756

(22) PCT Filed: Nov. 10, 2006

(86) PCT No.: PCT/NL2006/000542
§ 371 (c)(1), (2), (4) Date: Apr. 15, 2009

(87) PCT Pub. No.: WO2007/055563
PCT Pub. Date: May 18, 2007

(65) Prior Publication Data
US 2009/0306026 A1   Dec. 10, 2009

(30) Foreign Application Priority Data

Nov. 11, 2005  (EP) .................................... 05077577

(51) Int. Cl.
*A01N 45/00* (2006.01)
*A61K 31/56* (2006.01)
*A61K 31/4985* (2006.01)
*A61K 31/519* (2006.01)
*A61K 31/568* (2006.01)

(52) U.S. Cl.
CPC ........... *A61K 31/4985* (2013.01); *A61K 31/519* (2013.01); *A61K 31/568* (2013.01)

(58) Field of Classification Search
USPC ............................................... 514/169, 171
See application file for complete search history.

(56) References Cited

U.S. PATENT DOCUMENTS

| | | | |
|---|---|---|---|
| 3,976,776 A | 8/1976 | Wu et al. | |
| 4,521,421 A | 6/1985 | Foreman | |
| 4,596,795 A | 6/1986 | Pitha | |
| 4,640,921 A | 2/1987 | Othmer et al. | |
| 4,833,142 A | 5/1989 | Hartog et al. | |
| 4,877,774 A | 10/1989 | Pitha et al. | |
| 5,015,646 A | 5/1991 | Simms | |
| 5,250,534 A | 10/1993 | Bell et al. | |
| 5,389,687 A | 2/1995 | Schaus et al. | |
| 5,565,466 A | 10/1996 | Gioco et al. | |
| 5,731,339 A | 3/1998 | Lowrey | |
| 5,877,216 A | 3/1999 | Place et al. | |
| 6,165,975 A | 12/2000 | Adams et al. | |
| 6,242,436 B1 | 6/2001 | Llewellyn | |
| 6,246,436 B1 | 6/2001 | Lin et al. | |
| 6,251,436 B1 | 6/2001 | Drizen et al. | |
| 6,294,550 B1 | 9/2001 | Place et al. | |
| 6,306,841 B1 | 10/2001 | Place et al. | |
| 6,423,683 B1 | 7/2002 | Heaton | |
| 6,428,769 B1 | 8/2002 | Rubsamen et al. | |
| 6,469,012 B1 | 10/2002 | Ellis et al. | |
| 6,469,016 B1 | 10/2002 | Place et al. | |
| 6,472,434 B1 | 10/2002 | Place et al. | |
| 6,541,536 B2 | 4/2003 | Weikard et al. | |
| 6,593,313 B2 | 7/2003 | Place et al. | |
| 6,608,065 B1 | 8/2003 | Daugan | |
| 6,610,652 B2 | 8/2003 | Adams et al. | |
| 6,632,419 B2 | 10/2003 | Rubsamen et al. | |
| 6,964,780 B1 | 11/2005 | King et al. | |
| 7,151,103 B2 | 12/2006 | Borsini et al. | |
| 7,198,801 B2 | 4/2007 | Carrara et al. | |
| 2002/0002973 A1 | 1/2002 | Rubsamen et al. | |
| 2003/0022877 A1 | 1/2003 | Dudley | |
| 2003/0027804 A1 | 2/2003 | van der Hoop | |
| 2003/0104980 A1 | 6/2003 | Borsini et al. | |
| 2003/0139384 A1 | 7/2003 | Dudley | |
| 2004/0014761 A1* | 1/2004 | Place et al. ................... 514/247 |
| 2004/0186086 A1 | 9/2004 | Bunschoten et al. | |
| 2004/0208829 A1 | 10/2004 | Rubsamen et al. | |
| 2005/0152956 A1 | 7/2005 | Dudley | |
| 2005/0245539 A1 | 11/2005 | Mendla et al. | |
| 2006/0040935 A1 | 2/2006 | Maytom et al. | |
| 2006/0270642 A1 | 11/2006 | Lehman et al. | |
| 2006/0281752 A1 | 12/2006 | Heaton et al. | |
| 2006/0287335 A1 | 12/2006 | Sukoff Rizzo et al. | |
| 2007/0093450 A1 | 4/2007 | Tuiten | |
| 2007/0149454 A1 | 6/2007 | Mattern | |
| 2007/0154533 A1 | 7/2007 | Dudley | |
| 2009/0306026 A1 | 12/2009 | Tuiten et al. | |
| 2010/0093680 A1 | 4/2010 | Tuiten et al. | |
| 2010/0152145 A1 | 6/2010 | Tuiten et al. | |
| 2010/0160270 A1 | 6/2010 | Tuiten et al. | |

FOREIGN PATENT DOCUMENTS

| AU | 200062635 | 6/2005 |
|---|---|---|
| EP | 2000143 | 12/2008 |

(Continued)

OTHER PUBLICATIONS

Tuiten et. al. (Archives of general Psychiatry (2000) 57:149-153).*
International Search Report for PCT/NL2005/000355, mailed on Dec. 18, 2006, 5 pages.
Kuhn, Rec. Progress Hormone Research (2002) Academic Press vol. 57, pp. 411-434.
Shifren et al., New England Journal of Medicine (2000) 343:682-688.
Spungen et al., The Mount Sinai Journal of Medicine (1999) 66:201-205.

(Continued)

*Primary Examiner* — Marcos Sznaidman
(74) *Attorney, Agent, or Firm* — Morrison & Foerster LLP

(57) ABSTRACT

The invention relates to the field of female sexual dysfunction. It specifically relates to the influence of the combination of testosterone or an analog thereof and tadalafil on sexual health in female subjects with Female Sexual Dysfunction (such as Female Sexual Arousal Disorder (FSAD) or Female Sexual Desire Disorder (FSDD)). It further relates to the influence of the combination of testosterone or an analog thereof and a compound capable of at least in part inhibiting smooth muscle constriction, for example a compound capable of at least in part inhibiting the adrenergic tone. The invention further discloses other combinatorial therapies in the treatment of Female Sexual Dysfunction.

7 Claims, No Drawings

(56) References Cited

FOREIGN PATENT DOCUMENTS

| | | |
|---|---|---|
| JP | 11-504902 | 5/1999 |
| JP | 2001-520999 | 11/2001 |
| JP | 2002-543128 | 12/2002 |
| JP | 2003-530430 | 10/2003 |
| JP | 2004-520320 | 7/2004 |
| JP | 2005-500347 | 1/2005 |
| JP | 2005-503374 | 2/2005 |
| NZ | 524601 | 4/2006 |
| RU | 2130776 | 5/1999 |
| RU | 97117167 | 10/1999 |
| RU | 2152787 | 7/2000 |
| RU | 2180591 | 3/2002 |
| RU | 2285519 | 10/2006 |
| WO | WO-94/28902 | 12/1994 |
| WO | WO-95/05188 | 2/1995 |
| WO | WO-95/33486 | 12/1995 |
| WO | WO-96/28142 | 9/1996 |
| WO | WO-96/33705 | 10/1996 |
| WO | WO-96/36339 | 11/1996 |
| WO | WO-97/03675 | 2/1997 |
| WO | WO 99/21562 | 5/1999 |
| WO | WO-99/62502 | 9/1999 |
| WO | WO 00/66084 * | 5/2000 |
| WO | WO 00/66084 * | 11/2000 |
| WO | WO 00/66084 A | 11/2000 |
| WO | WO-00/66114 | 11/2000 |
| WO | WO-01/78703 | 10/2001 |
| WO | WO-02/26214 | 4/2002 |
| WO | WO-02/051420 | 7/2002 |
| WO | WO-02/069906 | 9/2002 |
| WO | WO-03/011300 | 2/2003 |
| WO | WO-03/011301 | 2/2003 |
| WO | WO 03002123 A2 | 9/2003 |
| WO | WO-2004/037173 | 5/2004 |
| WO | WO-2004/037262 | 5/2004 |
| WO | WO-2005/007166 | 1/2005 |
| WO | WO-2005/039530 | 5/2005 |
| WO | WO-2005/094827 | 10/2005 |
| WO | WO-2005/102342 | 11/2005 |
| WO | WO 2005/107810 | 11/2005 |
| WO | WO 2005/107810 A2 | 11/2005 |
| WO | WO-2006/127057 | 11/2006 |
| WO | WO-2007/054791 | 5/2007 |
| WO | WO 2007/055563 A2 | 5/2007 |

OTHER PUBLICATIONS

Berman et al., Safety and efficacy of sildenafil citrate for the treatment of female sexual arousal disorder: A double-blind, placebo controlled study, Journal of Urology, Dec. 2003, pp. 2333-2338, vol. 170, No. 6, Part 1.

Traish et al., Female genital sexual arousal: Biochemical mediators and potential mechanisms of dysfunction, Drug Discovery Today: Disease Mechanisms 2004, 2004, pp. 91-97, vol. 1, No. 1, United Kingdom.

Fourcroy et al., Female sexual dysfunction: Potential for pharmacotherapy, Drugs, 2003, pp. 1445-1457, vol. 63, No. 14.

PCT International Search Report, PCT/NL2006/000542 dated Jul. 17, 2007.

Belikov et al., Pharmaceutical Chemistry (1993) 43-47 (machine translation provided).

Doggrell, "Comparison of Clinical Trials with Sildenafil, Vardenafil and Tadalafil in Erectile Dysfunction," Expert Opin. Pharmacother. (2005) 6(1):1-2. (abstract).

Dyson et al., May's Chemistry of Synthetic Drugs, (5$^{th}$ ed. 1959) (machine translation provided).

Frye et al., "Behavioral Effects of 3 Alpha-Androstanediol.1: Modulation of Sexual Receptivity and Promotion of GABA-Stimulated Chloride Flux," Behav. Brain Res. (1996) 79 (1-2):109-118. (abstract).

Graham-Smith et al., Oxford Handbook of Clinical Pharmacology and Pharmacotherapy (2000) 18-20 (machine translation provided).

Haensel et al., "Flesinoxan: A Prosexual Drug for Male Rats," European Journal of Pharmacology (1997) 330:1-9.

Kharkevich et al., Pharmacology (3$^{rd}$ ed. 1987) 41-42 (machine translation provided).

Koolman et al., Biochemistry (1998) 365 (machine translation provided).

Phillips, "Female Sexual Dysfunction: Evaluation and Treatment," Am Fam Physician (2000) 62(1): 127-136, 141-142.

Rendell et al., "Sildenafil for Treatment of Erectile Dysfunction in Men with Diabetes A Randomized Controlled Trial," JAMA (1999) 281(5):421-426.

Sher et al., "Vaginal Sildenafil (Viagra): A Preliminary Report of a Novel Method to Improve Uterine Artery Blood Flow and Endometrial Development in Patients Undergoing IVF," Human Reproduction (2000) 15(4):805-809.

Shields et al., "Use of Sildenafil for Female Sexual Dysfunction," Ann. Pharmacother. (2006) 40:931-934.

The Merck Manual of Diagnosis and Therapy 30-36 (Robert Berkow, M.D. et al. eds., Merck Research Laboratories, Merck & Co., Inc. 1992) (1997) (machine translation provided).

The RLS Encyclopedia of Drugs, RLS 2004, vol. 11 (machine translation provided).

Tuiten et al., "Time Course of Effects of Testosterone Administration on Sexual Arousal in Women," Arch. Gen. Psychiatry (2000) 57:149-153.

Vidal's Handbook, Drugs in Russia, Moscow AstraPharmService 2001 (machine translation provided).

Morali et al., (1994) "Mechanisms Regulating Male Sexual Behavior in the Rat: Role of 3α-and 3β-Androstanediols," Biology of Reproduction 51:562-571.

Rasio-Filho et al. (1996) "Effects of 8-OH_DPAT on Sexual Behavior of Male Rats Castrated at Different Ages," Hormones and Behavior 30:251-258.

Singh et al. (2006) "Pharmokinetics of a Testosterone Gel in Healthy Postmenopausal Women," The Journal of Clinical Endocrinology & Metabolism 91(1):136-144.

International Preliminary Report on Patentability for International Patent Application No. PCT/NL2007/050533, mailed Jul. 2, 2009, 8 pages.

International Search Report for International Patent Application No. PCT/NL2007/050533, mailed Feb. 25, 2009, 3 pages.

International Preliminary Report on Patentability for International Patent Application No. PCT/NO2007/050534, mailed Jul. 2, 2009, 8 pages.

International Search Report for International Patent Application No. PCT/NO2007/050534, mailed Feb. 24, 2009, 3 pages.

International Preliminary Report on Patentability for International Patent Application No. PCT/NO2007/050535, mailed Jul. 2, 2009, 9 pages.

International Search Report for International Patent Application No. PCT/NO2007/050535, mailed Feb. 24, 2009, 3 pages.

Written Opinion of the International Searching Authority for PCT/NL2007/050533, issued May 5, 2009, 5 pages.

Ansel, "The Prescription," in Remington's Pharmaceutical Sciences, 17th Ed. (1985), Gennaro, (ed.), Chapter 101, pp. 1778-1787.

Holterhus et al., "Anabolic steroids, testosterone-precursors and virilizing androgens induce distinct activation profiles of androgen responsive promoter constructs," J Steroid Biochem Mol Biol (2002) 82:269-275.

Amstislavskaya et al., "Effect of serotonin 5-HT1A receptor agonists on sexual motivation of male mice," Bull Exp Biol Med (1999) 127(2):203-205.

Ottani et al., "Modulatory activity of sildenafil on copulatory behavior of both intact and castrated male rats," Pharmacology, Biochemistry and Behavior (2002) 72:717-722.

Angulo et al., "Vardenafil enhances clitoral and vaginal blood flow responses to pelvic nerve stimulation in female dogs," Int J Impot Res (2003) 15(2):137-141.

Kurashina et al., Pharmaceutical Society of Japan, Pharmacia (1999) 35(8):820.

Sipski et al., "Sildenafil effects on sexual and cardiovascular responses in women with spinal cord injury," Urology (2000) 55(6):812-815.

* cited by examiner

PHARMACEUTICAL FORMULATIONS AND USES THEREOF IN THE TREATMENT OF FEMALE SEXUAL DYSFUNCTION

CROSS-REFERENCE TO RELATED APPLICATIONS

This application is the National Phase entry under 35 U.S.C. §371 of PCT International Application Number PCT/NL/2006/000542, filed on Nov. 10, 2006, and published, in English, as WO 2007/055563 A2 on May 18, 2007, which itself claims priority to EP 05077577.4 filed Nov. 11, 2005.

The invention relates to the field of female sexual dysfunction. It specifically relates to the influence of the combination of testosterone or an analogue thereof and tadalafil on sexual health in female subjects with Female Sexual Dysfunction (such as Female Sexual Arousal Disorder (FSAD) or Female Sexual Desire Disorder (FSDD)). It further relates to the influence of the combination of testosterone or an analogue thereof and a compound capable of at least in part inhibiting smooth muscle constriction, for example a compound capable of at least in part inhibiting the adrenergic tone. The invention further discloses other combinatorial therapies in the treatment of Female Sexual Dysfunction.

Female Sexual Dysfunction (FSD) refers to various disturbances or impairments of sexual function, including a lack of interest in sexual activity, repeated failure to attain or maintain sexual excitement, inability to attain an orgasm following sufficient arousal. A recent study estimated that 43% of women suffer from sexual dysfunction in the USA[1]. Low sexual desire (22% prevalence) and sexual arousal problems (14% prevalence) belong to the most common categories of sexual dysfunction of women. These categories are convenient in providing working definitions and an accepted lexicon for researchers and therapists. However, it may be incorrect to assume that these disorders are fully independent of each other. Both case studies and epidemiological studies demonstrate that these disorders can overlap and may be interdependent. In some cases, it may be possible to identify the primary disorder that led to the others, but in many cases, this may be impossible.

In several studies it has been shown that selective type 5 phosphodiesterase (PDE5) inhibitors improve erectile function in men with erectile dysfunction, on average close to normal function[15]. In the penis, nitric oxide (NO) released from nerves and endothelium, induces production of cyclic guanosine monophosphate (cGMP). cGMP is a key mechanism in relaxing smooth muscle, necessary for the induction of an erection. This nucleotide is hydrolyzed by the phosphodiesterases, from which the main activity in the corpora cavernosa is due to PDE5. Therefore, during sexual stimulation the action of NO/cGMP on erectile function will be enhanced by PDE5-inhibitors. The genitalia of both sexes have common embryological origins. Recently, it has been shown that the clitoris consists of an erectile tissue complex, which embeds the anterior vaginal wall (O'connel et al 1998). Clitoral erection and the anterior wall of the vagina are highly involved in female sexual arousal and response. It has recently been shown that sildenafil—a PDE5-inhibitor—improves sexual performance in sexual functional women. Furthermore, it has recently been found that smooth muscle relaxation and engorgement of the rat clitoris is caused by the same intra- and extracellular mechanisms as in penile erection (Gragasin, et al., 2004).

Although in both men and women similar specialized vascular mechanism are involved in the genital response, an increase in Vaginal Pulse Amplitude (VPA) cannot be considered to be the equivalent of an erection. A necessary but not sufficient condition for an erection is dilatation of arteries and resulting increased blood inflow. In the penis there are corpora (corpus cavernosa (two) and corpus spongiosum (one) containing small irregular compartments (vascular spaces). The smooth muscles in the cavernous sinusoidal walls are normally tonically constricted under the control of an active sympathetic (adrenergic) tone. Relaxation of cavernous smooth muscle of the corpora results in filling and enlargements of the compartments with blood, which will be accompanied by an erection. Although the precise mechanisms are unknown, sympathetic innervations and parasympathetic driven NANC (non cholinergic non adrenergic) nerve innervations (nitric oxide) are believed to be both principal mediators in relaxation of the corporeal smooth muscles. In the penis, sympathetic innervations of the blood vessels are sparse, while the trabecular smooth muscles are richly innervated by this system. In contrast, the blood vessels of the penis are richly innervated by the parasympathetic system, while innervations of the trabecular smooth muscles by this system are sparse. Consequently, there are relatively independent effects of these two parts of the peripheral nervous system on processes involved in the occurrence of an erection. Initiation of dilatation of the penile arteries and subsequent increase of blood flow to the cavernous tissue is regulated by the parasympathetic nervous system (initiation of an increase in this cholinergic activity depends on signals by the brain). However, without relaxation of the smooth muscles there will be no erection. Reduction of the sympathetic tone and consequent relaxation of smooth muscles appears to be a relatively independent prerequisite for the initiation of an erection. Thus, penile erection occurs in response to increased activity of the sacral parasympathetic innervations and a decreased activity of sympathetic pathways. In the penis, nitric oxide (NO) released from NANC nerves and endothelium, induces production of cyclic guanosine monophosphate (cGMP). cGMP is a key mechanism in relaxing smooth muscle, necessary for the induction of an erection. The production and release of NO might be influenced by a decrease in activity of the sympathetic branch, for example through the resulting reduction of heterotropic inhibition of the parasympathetic branch, which is mediated by the same post ganglionic sympathetic ganglion.

For the treatment of female sexual disorder a number of different treatments, with greater or lesser degrees of success have been suggested and applied. These treatments have either not been completely successful or the side effects are hardly acceptable. The present invention provides multiple new combinations of therapeutic substances, preferably given in a particular convenient dosage scheme, which combination is effective and does not have serious side effects.

Thus the invention provides the use of a combination of testosterone or an analogue thereof and tadalafil, in the preparation of a medicament for the treatment of female sexual dysfunction, wherein said testosterone or an analogue thereof and tadalafil are released at essentially the same time and wherein said testosterone or an analogue thereof is provided such that there is a peak of testosterone or an analogue thereof in the blood circulation of the subject to whom it is administered. According to this part of the invention, although it is not considered bound by theory, an effect on the central nervous system and the peripheral system are required, whereby the signal to the central system is provided by testosterone or an analogue thereof (having the same kind of activity) and the peripheral signal is provided by tadalafil. According to the invention the level of free testosterone should be a peak plasma level of free testosterone at least of about 0.010 nmol/

L, which will typically occur between 1 and 20 minutes after administration of the testosterone. About three and a half to five and a half hours after this plasma testosterone peak, there is a testosterone effect peak, i.e. there is a time lag in the effect of testosterone on genital arousal in sexually functional women. Until recently, it was thought that tadalafil should be administered a couple of hours after the testosterone to be at least partly effective in the treatment of FSD. However, it is now disclosed that testosterone or an analogue thereof and tadalafil may be released at essentially the same time (resulting in an overlap of the effect of tadalafil and the effect of testosterone) and that this results in the treatment of FSD.

The term "essentially the same time" should be understood to mean that preferably testosterone or an analogue thereof and tadalafil are released within the to be treated subject within 30 minutes from each other, preferably 25-30 minutes, more preferably 20-25 minutes, even more preferably 15-20 or 10-15 minutes and most preferably the two compounds are released in the subject within 5 to 10 minutes from each other.

Depending on the formulation of testosterone or an analogue thereof and depending on the formulation of tadalafil there are different possibilities. For example testosterone (or an analogue thereof) and tadalafil are both formulated to provide release of the active compound a couple of hours (for example 2 hours) after administration (i.e. delayed release) in such a way that they are released at essentially the same time, for example within 30 minutes from each other. If testosterone (or an analogue thereof) and tadalafil are formulated in such a way, the formulations must be taken at least 3-4½ hours plus the release time (in this example 2 hours) before sexual activity. It is clear to the skilled person that dependent on the amount of time used/taken for sexual activity, variations on the exact moment of administration of the formulations is possible. These variants are embraced in the present invention. However, it is also possible to formulate testosterone (or an analogue thereof) and tadalafil such that they are essentially both released upon administration. In such a case, the formulations must be taken approximately 3-4½ hours before sexual activity. Moreover, testosterone (or an analogue thereof) and tadalafil can be formulated separately (in which case the formulations can be taken at the same time or subsequently) or the compounds can be formulated in one and the same formulation in which case the compounds are taken at the same time. It should be clear to the skilled person that a variety of changes can be made to the formulations which are all within the scope of the present invention. In a preferred embodiment, testosterone (or an analogue) thereof and tadalafil are administered or taken at the same time, thereby reducing the risk of forgetting to take one of the formulations (at all or in time) and thus increasing the change of an effective treatment. However, it is clear that in case the to be treated female subject is very accurate in respect of taking medications, testosterone (or an analogue thereof) and tadalafil may also be taken separately in time. In the above-described embodiments, care must be taken that the release of the active ingredients (i.e. tadalafil and testosterone) are such that they are released at essentially the same time.

Now that we know that the effect of tadalafil is present for 12-36 hours, it is also possible to first release tadalafil and later on testosterone. Preferably, testosterone is released at the latest 3-4½ hours before the effect of tadalafil starts decreasing which is approximately after 12-24 hours.

Hence, in yet another embodiment, the invention provides use of a combination of testosterone or an analogue thereof and tadalafil, in the preparation of a medicament for the treatment of FSD, wherein tadalafil is released or administered in a subject prior to testosterone or an analogue thereof and wherein said testosterone or an analogue thereof is provided such that there is a peak of testosterone or an analogue thereof in the blood circulation of the subject to whom it is administered. Preferably, tadalafil is released 2-14 hours, more preferably 4-12 hours and most preferably 6-10 hours prior to testosterone or an analogue thereof. Such an approach is very useful for sexual activity in the morning. The evening prior to the desired sexual activity, tadalafil is administrated/taken in such a formulation that it is released upon administration or within for example 1 hour. Testosterone is provided such that it is released after 6-10 hours. The release is arranged such that 3 to 4½ hours later, the female in question awakes and is primed for sexual activity.

Testosterone is preferably given in a formulation wherein there is a (short-lasting) (high, i.e. 10-100 times increase of normal testosterone serum levels) peak of testosterone in the blood circulation of the subject to whom it is administered. The term "short-lasting" means that there is a sharp increase of the serum testosterone level and approximately 1-20 minutes after administration a peak serum level of testosterone is obtained. The peak serum level sharply decreases and after approximately 120 minutes the testosterone serum level is back to the level before testosterone administration. The invention therefore provides a use, wherein the testosterone or an analogue thereof is provided in the form of a sublingual formulation, preferably a sublingual formulation comprising cyclodextrins as carrier. Another example of a suitable route of administration is buco-mucosally or intranasally, which can also be performed with the use of a cyclodextrin formulation or other usual excipients, diluents and the like. A typical example of a formulation is given in hydroxypropyl-beta cyclodextrin, but other beta cyclodextrins and other usual excipients, diluents and the like are within the skill of the art for preparing a formulation comprising testosterone or an analogue thereof, which releases essentially all of the testosterone within one short burst. Said burst will typically be within a short time interval (for example within 60-120 seconds, more preferably within 60 seconds) upon administration, leading to blood peak levels of testosterone about 1-20 minutes later. In a preferred embodiment, the pharmaceutical is designed for sublingual administration and even more preferred said composition comprises cyclodextrin such as hydroxypropyl-beta cyclodextrin. A typical example of a prepared testosterone sample (for 0.5 mg of testosterone) consists of 0.5 mg testosterone, 5 mg hydroxypropyl-betacyclodextrines (carrier), 5 mg ethanol, and 5 ml water, but each of the amounts of these substances might be higher or lower.

Testosterone in the circulation is typically bound by SHBG (steroid hormone binding globulin) and by albumin. It is important that the peak plasma level of testosterone as defined in the present invention is present and calculated as free testosterone, so a fraction not bound by albumin and SHBG. Thus the dose of testosterone given should be high enough to saturate the albumin and SHBG (i.e the concentration of testosterone must be high enough to overcome complete binding of testosterone by SHBG or albumin), or another way of avoiding binding to albumin or SHBG must be designed, such as the use of a competitor for the testosterone binding site on SHBG.

For the present invention the routes of administration of choice are those which are the least invasive (for example oral, buco-mucosal or intranasal). Motivation for sexual behaviour should not be negatively influenced by invasive routes of administration.

The invention also provides a kit of parts comprising at least one pharmaceutical composition comprising testosterone or an analogue thereof and at least one pharmaceutical composition comprising tadalafil wherein said kit further comprises instructions in respect to the administration of said compositions, preferably the kit comprises instructions to administer said compositions at essentially the same time or said kit comprises instructions to first administrate tadalafil and later on testosterone.

In a preferred embodiment, said composition comprising testosterone is designed to release all testosterone essentially immediately (for example within 60 seconds) at the target site. Said kit preferably contains instructions to use a pharmaceutical composition comprising testosterone and a pharmaceutical comprising tadalafil 3.5-4.5 hours prior to sexual activity. It is clear to the skilled person that the kit of parts contains an effective amount of each active ingredient. The kit of parts may comprise a sublingual formulation of testosterone or an analogue thereof and a tablet or another formulation comprising tadalafil. The amount of testosterone per pharmaceutical composition comprising testosterone is at least 0.3 mg testosterone and at most 2.5 mg testosterone. Higher or lower doses may be necessary depending on the albumin and SHBG levels and the weight of the subject to be treated. The pharmaceutical composition comprising tadalafil comprises at least 5 mg tadalafil and at most 20 mg tadalafil. Again this dose may vary with the weight of the patient. For the reasons already outlined above, a kit according to the invention may further comprise a compound capable of competing with testosterone (or an analogue thereof) for SHBG binding.

Testosterone is also known under the chemical name 17-β-hydroxyandrost-4-en-3-one which can be obtained in various ways: it may be isolated and purified from nature or synthetically produced by any manner. The term "or an analogue thereof" includes any useful metabolite or precursor of testosterone, for example the metabolite dihydrotestosterone. If an analogue of testosterone is used, the herein described timeframes might be subject to some change, but this can easily be ascertained by the skilled person without any undue burden.

Tadalafil is chemically designated as pyrazino[1',2':1,6]pyrido[3,4-b]indole-1,4-dione, 6-(1,3-benzodioxol-5-yl)-2,3,6,7,12,12a-hexahydro-2-methyl-, (6R,12aR)-. In addition to the active ingredient, tadalafil, each tablet contains the following ingredients: croscarmellose sodium, hydroxypropyl cellulose, hypromellose, iron oxide, lactose monohydrate, magnesium stearate, microcrystalline cellulose, sodium lauryl sulfate, talc, titanium dioxide, and triacetin. As already outlined above, the tablets can be taken as such or are formulated in a for example slow-release formulation.

In order to further enhance the effects of the kit of parts of the invention said kit may further comprise means for cognitive interventions and stimulation. Such information may be present on any data carrier (paper, CD, DVD), passive or interactive, or it may be a link to a website at least partially designed for the purpose of said cognitive stimulation. Sometimes it is preferred to present said cognitive stimulatory information subconsciously e.g. subliminally.

To further enhance the effects of the kit of the present invention a substance may be added to said kit which stimulates the mesolimbic dopaminergic pathway in the subject. This pathway is concerned with a relatively different kind of reward system which helps providing an increase in reward-seeking involved in sexual behaviour. Examples of such compounds are Apomorphine, a dopamine D2 agonist; Aripiprazole, a partial dopamine D2 agonist; Pergolide, a nonselectieve dopamine (DA) agonist; Pramipexole, a new dopamine receptor agonist with preference for D3 compared to D2 and D4 receptors; Bromocriptine, a nonselectieve dopamine (DA) agonist; Ropinirole hydrochloride, a non-ergoline dopamine agonist with a relatively high in vitro specificity and full intrinsic activity at the $D_2$ and $D_3$ dopamine receptor subtypes; it binds with higher affinity to $D_3$ than to $D_2$ or $D_4$ receptor subtypes; Roxindole, a potent (autoreceptor)-"selective" D3 dopamine agonist; Cabergoline, a dopamine D2 agonist; Lisuride, a nonselectieve dopamine (DA) agonist, and the autoreceptor antagonists; (+)-AJ 76, a D3-preferring, dopamine (DA) autoreceptor antagonist; (+)-UH232, a stimulant of dopaminergic transmission, which may preferentially antagonize autoreceptors of dopamine nerve terminals, as well as the reuptake blockers; Bupropion, an inhibitor of the neuronal uptake of norepinephrine, serotonin and dopamine; Amineptine, a (relatively) selective dopamine reuptake inhibitor; GBR 12909 (vanoxerine), a dopamine reuptake inhibitor; and Amantadine; a NMDA receptor antagonist and dopamine reuptake inhibitor.

To further enhance the effects of the kit of the present invention a substance is (optionally) added which inhibits the central and peripheral adrenergic tone, i.e. inhibits or dampens central and peripheral extracellular norepinephrine concentrations. Activation of alpha 2 adrenoreceptors located in the central nervous system results in inhibition of sympathetic tone. Examples of such compounds are clonidine, an alpha 2 adrenoreceptor agonist; imidazoline, a partial alpha 2 adrenoreceptor agonist; and dexmedetomidine, an alpha 2 adrenoreceptor agonist. Antagonism of alpha 1 adrenergic receptors in the periphery blocks the effects of the adrenergic tone (norepinephrine). Examples of such compounds are Prazosin, thymoxamine (moxisylyte), NMI-870, HMP12 or phentolamine Low sexual desire, sexual arousal problems and hampered orgasm are candidates for psychopharmacological treatment. These categories of sexual problems are also linked to three (transitional and overlapping) phases of the human sexual response (sexual desire, sexual arousal and orgasm), which are regulated by relatively independent neurotransmitter functions. Traditionally, motivated behaviours have been divided into appetitive and consummatory components. Activities aimed at obtaining reward and satisfaction belong to the appetitive component. The fundamental appetitive motivational process is an intrinsic brain function, and is especially related to the predictive value of stimuli for reward. Processing of motivationally relevant information (i.e. stimuli predicting reward) causes an increase in activity of the meso-accumbens dopaminergic (DA) system (i.e. DA neurons of the ventral tegmental area (VTA) innervating the nucleus accumbens (NAS)), a component of the mesolimbic dopamine system. The activity of this system is increased during flexible approach behaviour when anticipating reward related to copulation[2]. Increasing activity in these dopaminergic pathways facilitates sexual motivation, in particular anticipatory sexual behavior[3]. Aripiprazole is, among others, an example of a drug which influences dopaminergic pathways, and which may be used in combination with testosterone or an analogue thereof and a PDE5-inhibitor to affect sexual motivation and behaviour. Aripiprazol is a high-affinity partial agonist of the dopamine D2 receptor and serotonin 5-HT1a receptor, and antagonist of the 5-HT2a receptor. Aripiprazol is described as a dopamine system stabilizer which is due to its partial agonistic actions at the D2 receptor, especially the presynaptic D2 receptors, for which it has higher affinity. Stimulation of autoreceptors located on dopamine nerve terminals results in an inhibition of dopamine synthesis and release. Thus, in a low dopaminergic state of the meso-accumbens DA system, aripiprazol would antagonize presynaptic D2 receptors, freeing the NAS-projecting DA nuclei in the VTA from autoinhibition. The medial prefrontal cortex (mPFC) mediates behavioural inhibition. Dopamine in the mPFC plays an important role in behavioural inhibition. Illustrative of mPFC-DA's inhibitory role is the inhibition of the meso-accumbens DA system; high extracellular concentrations of mPFC-DA inhibit meso-accumbal DA activity, and low extracellular concentrations of mPFC-DA activate meso-accumbal DA activity through disinhibition. It is therefore conceivable that a dopaminergic role in FSD is not restricted to meso-accumbal DA, but extendable to mPFC-DA, where symptoms of FSD are enhanced with high activity of mPFC-DA, albeit via inhibition of accumbal DA or via inhibition of other cognitive or emotional factors involved in FSAD. The partial agonistic action of aripiprazol will then have a positive effect on alleviation of FSD (symptomatology) through agonism of presynaptic D2 receptor in the mPFC, thereby inhibiting DA release in this area. Anticipating sexual reward will produce arousal of the genitalia, in which at least three key neurotransmitters are involved: acetylcholine, norepinephrine and nitric oxide. Acetylcholine and nitric oxide both promote erections in men and lubrication and swelling in women. Norepinephrine inhibits erections in men and lubrication and swelling in women. Orgasm, the consummatory phase of human sexual response is facilitated by descending spinal noradrenergic fibers and innervation of the genitalia, and inhibited by descending spinal serotonergic fibers.

The kit of parts is useful for any individual suffering from any form of FSD, be it through psychological or physiological causes or combinations thereof. It is thus also useful for subjects having FSD because of other medicines and/or drugs—such as SSRI's—; subjects suffering from hypogonadism, etcetera.

Treatments with a dosage of testosterone combined with tadalafil produce alterations in brain and bodily functions which will make learning of positive associations between sexual stimuli, genital arousal and subjective experience possible. Moreover, the treatment of FSD with a combination of testosterone and tadalafil is preferably augmented by an "approach induction" treatment. To create a more permanent psychological change, the central en bodily processes activated by testosterone and tadalafil under sexually relevant stimulation need to be perceived and need to become associated with a positive hedonic tone or with activation of the behavioral approach system. The perception of bodily reactions by focusing attention on genital arousal is made possible by testosterone (whereby the genital arousal is synergistically enhanced by tadalafil) and can be emphasized by verbal instructions. A positive hedonic tone cannot be taken for granted in the population of FSD patients. In order to achieve a positive tone, patients can be exposed to positive stimuli during the effective phase of the drugs (that is, at least 3 hours after testosterone intake). These positively motivated stimuli consist of pictures of happy faces of persons of the patient's sexually preferred gender, possibly including the face of the partner. The pictures of the faces are presented subliminally, so that in an unobtrusive way the behavioral approach system becomes activated.

The treatment of FSD might consist of creating a situation in which the patient learns to associate genital arousal with a positive hedonic tone or activation of the behavioral approach system. This requires inducement of genital arousal (by sexual stimuli and tadalafil), sustained attention to sexual stimuli and to genital arousal (made possible by testosterone) and activation of the behavioral approach system (by subliminal presentation of pictures of happy faces).

The invention further provides a method for treating a female suffering from female sexual dysfunction by providing to said female a combination of tadalafil and testosterone or an analogue thereof.

Besides the use of testosterone (or an analogue thereof) and a PDE5-inhibitor in general and tadalafil in specific, combinations of testosterone (or an analogue thereof) with at least one other compound is also suitable in the treatment of FSD. One example of a PDE5-inhibitor replacement is a compound which is at least capable of partly inhibiting smooth muscle constriction in general and preferably is a compound which is at least capable of partly inhibiting (or dampening) the adrenergic tone. Inhibition or dampening of the adrenergic tone should be read to result in: (i) a decrease in the amount of available norepinephrine at the adrenoreceptors (for example by inhibiting norepinephrine synthesis or emission through autoreceptor agonism) and/or (ii) a decrease in the effect of the available norepinephrine at the postsynaptic adrenoreceptor (for example by blocking postsynaptic adrenergic receptors), and/or (iii) a decrease in the effect of postsynaptic adrenoreceptor activation (for example, by interfering downstream of norepinephrine). In yet another embodiment, the invention therefore provides the use of a combination of testosterone or an analogue thereof and a compound capable of at least in part inhibiting the adrenergic tone, in the preparation of a medicament for the treatment of FSD, wherein said testosterone or an analogue thereof is provided such that there is a peak of testosterone or an analogue thereof in the blood circulation of the subject to whom it is administered. In a preferred embodiment, said compound capable of at least in part inhibiting the adrenergic tone is an alpha1-adrenoceptor antagonist, such as Prazosin, thymoxamine (moxisylyte), NMI-870, HMP12 or phentolamine, or alpha 2 adrenoreceptor agonists, such as clonidine (an alpha 2 adrenoreceptor agonist), imidazoline (a partial alpha 2 adrenoreceptor agonist) or dexmedetomidine (an alpha 2 adrenoreceptor agonist). Examples of compounds capable of at least in part inhibiting smooth muscle constriction are a Rho kinase antagonist, a Neuropeptide Y antagonist or an Angiotensin II antagonist.

Suitable concentrations and formulations of testosterone (or an analogue thereof) are as outlined above.

It is clear to the skilled person that the above mentioned compounds (for example the mentioned adrenoceptor antagonists) must be dosed and released in such a way that their effect at least partly coincide with the effect of testosterone, i.e. the effect of said compounds must be present 3.5-5.5 hours after the release of testosterone (or an analogue thereof). The skilled person can, based on the pharmacological kinetics of said compounds, easily determine a suitable formulation as well as a suitable concentration for said compounds.

PDE5 is part of the parasympathetic chain and the presence of PDE5 results in inhibition of smooth muscle relaxation and thus subsequently contraction of smooth muscle tissue. Inhibition of PDE5 via PDE5-inhibitors is one way in which FSD can be treated. It is however also possible to facilitate a parasympathetically driven response (i.e facilitation of smooth muscle relaxation) by using compounds such as an organic nitrate (for example nitroglycerin which is a guanylyl cyclase stimulant), a K+ channel opener (for example BMS-2231321), a PGE1 agonist (for example alprostadil or prostacycline or a Vasoactive Intestinal Polypeptide (VIP) agonist (for example aviptadil) or by administering nitric oxide (for example via inhalation) or L-arginine glutamate (precursor of NO).

The invention further provides use of testosterone (or an analogue thereof) in combination with any of the above-mentioned compounds (for example a compound capable of at least in part inhibiting or dampening the adrenergic tone) in combination with a PDE5-inhibitor, such as vardenafil, sildenafil or tadalafil or any of the other known PDE5-inhibitors. The amount of PDE5-inhibitors is still expanding and non-limiting examples are the following: E-4021, E-8010, E-4010, AWD-12-217 (zaprinast), AWD 12-210, UK-343, 664, UK-369003, UK-357903, BMS-341400, BMS-223131, FR226807, FR-229934, EMR-6203, Sch-51866, IC485, TA-1790, DA-8159, NCX-911 or KS-505a. Other examples can be found in WO 96/26940.

As already described tadalafil may be administered in such a way that it is released at the same time as testosterone. It may however also be provided as described below for vardenafil or sildenafil.

Vardenafil or sildenafil are preferably provided in such a way that their peak effect at least partly overlaps with the effect of testosterone. To obtain such an overlap, testosterone is provided first (preferably as a sublingual formulation) and vardenafil or sildenafil are preferably provided approximately 1.5-2.5 hours after the administration of the testosterone, even more preferably such that $C_{max}$ arises about 3 to 4 hours after the plasma free testosterone peak. This is for example realized by a sustained release version of sildenafil or vardenafil, or through a delayed release formulation.

A typical example for oral administration of vardenafil is given in vardenafil HCl which is designated chemically as piperazine, 1-[[3-(1,4-dihydro-5-methyl-4-oxo-7-propylimidazo[5,1-f][1,2,4]triazin-2-yl)-4-ethoxyphenyl]sulfonyl]-4-ethyl-, monohydrochloride. In addition to the active ingredient, vardenafil HCl, each tablet contains microcrystalline cellulose, crospovidone, colloidal silicon dioxide, magnesium stearate, hypromellose, polyethylene glycol, titanium dioxide, yellow ferric oxide, and red ferric oxide. An other example is given in sildenafil citrate which is chemically designated as 1-[[3-(6,7-dihydro-1-methyl-7-oxo-3-propyl-1Hpyrazolo[4,3-d]pyrimidin-5-yl)-4-ethoxyphenyl]sulfonyl]-4-methylpiperazine citrate. In addition to the active ingredient, sildenafil citrate, each tablet contains the following ingredients: microcrystalline cellulose, anhydrous dibasic calcium phosphate, croscarmellose sodium, magnesium stearate, hydroxypropyl methylcellulose, titanium dioxide, lactose, triacetin, and FD & C Blue #2 aluminum lake.

The amount of testosterone per pharmaceutical composition comprising testosterone is at least 0.3 mg testosterone and at most 2.5 mg testosterone. Higher or lower doses may be necessary depending on the albumin and SHBG levels and the weight of the subject to be treated. The pharmaceutical composition comprising a PDE5-inhibitor comprises at least 25 mg sildenafil (or 5 mg vardenafil, or 5 mg tadalafil) and at most 100 mg sildenafil (or 20 mg vardenafil, or 20 mg tadalafil), or comparable dosages of other PDE5-inhibitors. Again these doses may vary with the weight of the patient. For the reasons already outlined above, a kit according to the invention may further comprise a compound capable of competing with testosterone or an analogue thereof for SHBG binding).

The above mentioned combination of compounds (for example testosterone (or an analogue thereof) and a compound capable of at least in part inhibiting the adrenergic tone and optionally a PDE5-inhibitor) may conveniently be packed together as a kit of parts, preferably accompanied with instructions how and when to administrate the separate (or combined) compounds.

Such a kit may further comprise means for cognitive interventions directing attention to genital arousal during appropriate conditions for sufficient sexual stimulation or means for cognitive interventions inducing activation of the behavioural approach system or a positive hedonic tone by subliminal exposure to pictures of happy faces of persons of the patient's sexually preferred gender. Or a kit of parts may further comprise an agonist of the dopamine-pathway.

In the absence of PDE5-inhibitor, PDE5 binds to cGMP and inhibits the closing of calcium channels and opening of the potassium channels (i.e inhibits hyperpolarization of the smooth muscle), and thus it inhibits smooth muscle relaxation. The interaction between PDE5 and cGMP is accomplished by the interaction of the PDE5's GAF-A N-terminal domain which are a potential target for drug development. In yet another embodiment, the invention provides use of a combination of testosterone or an analogue thereof and a compound capable of at least in part inhibiting the interaction between a GAF-A domain and cGMP (for example a GAF-A blocker) in the preparation of a medicament for the treatment of female sexual dysfunction, wherein said testosterone or an analogue thereof is provided such that there is a peak of testosterone or an analogue thereof in the blood circulation of the subject to whom it is administered. The presence of for example a GAF-A blocker would at least partly prevent the binding of PDE5 to cGMP, resulting in smooth muscle cell relaxation.

Suitable formulations for testosterone (or an analogue thereof) are provided above.

It is clear to the skilled person that the compound capable of at least in part inhibiting the interaction between a GAF-A domain and cGMP (for example a GAF-A blocker) must be dosed and released in such a way that it's effect at least partly coincide with the effect of testosterone, i.e. the effect of said compounds must be present 3.5-5.5 hours after the induced plasma peak in testosterone (or an analogue thereof). The skilled person can, based on the pharmacological kinetics of said compound, easily determine a suitable formulation as well as a suitable concentration for said compounds.

The invention will be explained in more detail in the following, non-limiting examples.

EXPERIMENTAL PART

Experiment 1

Efficacy of Cyclodextrine-Bound Testosterone Administration in Combination with Tadalafil Administration on VPA in Response to Erotic Film Excerpts in Women with FSD In a double-blind, randomly assigned placebo controlled cross-over design, a group of 16 women with female sexual dysfunction (FSD) will receive tadalafil (10 mg) alone, sublingual cyclodextrin-bound testosterone (0.5 mg) alone, tadalafil and sublingual cyclodextrin-bound testosterone combined (resp. 10 mg & 0.5 mg) or a placebo during 4 separate experimental days. The vaginal pulse amplitude will be measured in response to neutral and erotic film excerpts, directly after drug administration, and 4 hours after drug administration. The four experimental days will be separated by (at least) a three-day period. On all drug administrations, subjects will receive one capsule consisting of either tadalafil or a placebo, and one liquid cyclodextrine suspension with or without testosterone (which is tasteless). Both will be taken at the same time. The time lag in effect of sublingual cyclodextrin-bound testosterone (approximately 4 hours) will overlap with high (approx >95% of tadalafil $C_{max}$) tadalafil serum concentrations ($T_{max}$ of tadalafil 2 hours; $T_{1/2}$=17.5 hours).

During the experimental session, the subject must insert the tampon-shaped vaginal probe (a photoplethysmograph) in order to measure the VPA. Then subjects will view a 10 minute neutral fragment, followed by a 5 minute erotic film fragment. After these baseline measurements, the subjects receive one of the four medication combinations as described above. Following medication another set of neutral (5 minutes) and erotic (5 minutes) film fragments is shown. The vaginal probe will then be removed. After 4 hours another VPA measurement will be made in response to neutral (5 minutes) and erotic (5 minutes) film fragments. Blood pressure (supine and standing), heart rate, respiration rate, and body temperature will be monitored throughout the experimental days.

The experimental will be preceded by a screening visit. In this screening visit subjects are interviewed and examined by a resident of the department of gynecology of Flevo Hospital, Almere to diagnose for FSD and to determine eligibility for study participation. Subjects will be asked to fill out a questionnaire; the Female Sexual Function Index (FSFI). Subjects will be screened to exclude pregnancy or breast feeding, vaginal infections, major operations to the vagina and/or vulva, undetected major gynecological illnesses or unexplained gynecological complaints. Weight, height, blood pressure (supine and standing) will be measured. Cardiovascular condition will be tested and ECG checked for significant abnormalities.

Subjects with a history of endocrinological, neurological or psychiatric illness and/or treatment. Standard blood chemistry and hematology tests will be performed. Participants are required not to use alcohol or psychoactive drugs the evening before and the day of experimentation. During period of menstruation, subjects will not be tested.

Experiment 2

Efficacy of Cyclodextrine-Bound Testosterone Administration in Combination with Prazosin Administration on VPA in Response to Erotic Film Excerpts in Women with FSD In a double-blind, randomly assigned placebo controlled cross-over design, a group of 16 women with female sexual dysfunction (FSD) will receive prazosin (0.5 mg) alone, sublingual cyclodextrin-bound testosterone (0.5 mg) alone, tadalafil and sublingual cyclodextrin-bound testosterone combined (resp. 0.5 mg & 0.5 mg) or a placebo during 4 separate experimental days. The vaginal pulse amplitude will be measured in response to neutral and erotic film excerpts, directly after drug administration, and 4 hours after drug administration. The four experimental days will be separated by (at least) a three-day period. On all drug administrations, subjects will receive one capsule consisting of either prazosin or a placebo, and one liquid cyclodextrine suspension with or without testosterone (which is tasteless). The time lag in effect of sublingual cyclodextrin-bound testosterone (approximately 4 hours) must overlap with high (approx >95% of prazosin $C_{max}$) prazosin serum concentrations ($T_{max}$ of prazosin 1-2 hours; $T_{1/2}$=2-3 hours). Therefore, prazosin must be administered in such a way, that prazosin $C_{max}$ arises about 3 to 4 hours after the plasma free testosterone peak. Therefore, prazosin must be administered approximately 2.5 hours after sublingual testosterone administration, or prazosin must be modified so that it is released at approximately 2.5 hours following administration, or so that $C_{max}$ arises about 3 to 4 hours after the plasma free testosterone peak.

In this experimental example, a prazosin delayed release (2.5 hours) formulation is used.

During the experimental session, the subject must insert the tampon-shaped vaginal probe (a photoplethysmograph) in order to measure the VPA. Then subjects will view a 10 minute neutral fragment, followed by a 5 minute erotic film fragment. After these baseline measurements, the subjects receive one of the four medication combinations as described above. Following medication another set of neutral (5 minutes) and erotic (5 minutes) film fragments is shown. The vaginal probe will then be removed. After 4 hours another VPA measurement will be made in response to neutral (5 minutes) and erotic (5 minutes) film fragments. Blood pressure (supine and standing), heart rate, respiration rate, and body temperature will be monitored throughout the experimental days.

The experimental will be preceded by a screening visit. In this screening visit subjects are interviewed and examined by a resident of the department of gynecology of Flevo Hospital, Almere to diagnose for FSD and to determine eligibility for study participation. Subjects will be asked to fill out a questionnaire; the Female Sexual Function Index (FSFI). Subjects will be screened to exclude pregnancy or breast feeding, vaginal infections, major operations to the vagina and/or vulva, undetected major gynecological illnesses or unexplained gynecological complaints. Weight, height, blood pressure (supine and standing) will be measured. Cardiovascular condition will be tested and ECG checked for significant abnormalities.

Subjects with a history of endocrinological, neurological or psychiatric illness and/or treatment. Standard blood chemistry and hematology tests will be performed. Participants are required not to use alcohol or psychoactive drugs the evening before and the day of experimentation. During period of menstruation, subjects will not be tested.

REFERENCES

1. Laumann, E. O., Paik. A. and Rosen, R. C.: Sexual dysfunction in the United States: prevalence and predictors. JAMA 10: 281, 537, 1999.
2. Ikemoto, S. & Panksepp J. The role of nucleus accumbens dopamine in motivated behaviour: a unifying interpretation with special reference to reward-seeking. Br Res Rev 31: 6-41, 1999.
3. Melis, M. R. & Argiolis, A. Dopamine and sexual behavior. Neurosc. Biobehavioural Reviews 19: 19-38, 1995.
15. Potempa, A J., Bernard I., and Ulbrich E. Under Flexible dosing, "Real world" condition PDE5 inhibitor improved erectile function in a broad population of men. Europ Urol Suppl. 2: 96, 2003. Klotz T., Sashe R., Heidrich A., et al. PDE5 inhibitor increases penile rigidity and tumescence in erectile dysfunction patients: a Rigiscan and pharmacokinetic study. World J Urol 19: 32-39.

O'Connell H E, Hutson J M, Anderson C R, et al: Anatomical relationship between urethra and clitoris. *J Urol* 159: 1892-1897, 1998.

Gragasin F S, Michelakis E D, Hogan A, Moudgil R, Hashimoto K, Wu X, Bonnet S, Haromy A, Archer S L. The neurovascular mechanism of clitoral erection: nitric oxide and cGMP-stimulated activation of BKCa channels. *FASEB J.* 2004 September; 18 (12):1382-91.

The invention claimed is:

1. A method for treating female sexual dysfunction, the method comprising:

administering to a female subject in need thereof a combination of tadalafil and testosterone or dihydrotestosterone (DHT),
at essentially the same time 3-5.5 hours before anticipated sexual activity, and
wherein said testosterone or DHT is provided such that there is a peak concentration of testosterone or DHT in the blood circulation of the subject to whom it has been administered,
wherein said testosterone or DHT and tadalafil are formulated to be released upon administration; and said testosterone or DHT is released in one short burst.

2. The method according to claim 1, wherein said essentially the same time is wherein said testosterone or DHT and tadalafil are released within 30 minutes of each other.

3. The method according to claim 1, wherein said tadalafil is administered orally, buco-mucosally, or intra-nasally.

4. The method according to claim 1, wherein said testosterone or DHT is administered sublingually, buco-mucosally or intranasally.

5. The method according to claim 4, wherein said testosterone or DHT is formulated in a cyclodextrin formulation.

6. The method according to claim 1, wherein 0.3-25 mg of testosterone is administered.

7. The method according to claim 1, wherein 5-20 mg of tadalafil is administered.

* * * * *